(12) United States Patent
Kushida

(10) Patent No.: US 7,318,643 B2
(45) Date of Patent: Jan. 15, 2008

(54) OPHTHALMIC IMAGE PICKUP APPARATUS, OPHTHALMIC IMAGE PICKUP METHOD AND OPHTHALMIC IMAGE PROCESSING SYSTEM

(75) Inventor: Akihiro Kushida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 325 days.

(21) Appl. No.: 11/227,000

(22) Filed: Sep. 14, 2005

(65) Prior Publication Data

US 2006/0077349 A1 Apr. 13, 2006

(30) Foreign Application Priority Data

Oct. 5, 2004 (JP) .............................. 2004-292502

(51) Int. Cl.
*A61B 3/10* (2006.01)

(52) U.S. Cl. ...................................... 351/205; 351/206
(58) Field of Classification Search ................ 351/205, 351/200–204, 206–213
See application file for complete search history.

(56) References Cited

U.S. PATENT DOCUMENTS 5,822,446 A 10/1998 Kato

FOREIGN PATENT DOCUMENTS

| JP | 63-156477 A | 6/1988 |
|----|-------------|--------|
| JP | 6-98859 A | 4/1994 |

*Primary Examiner*—Timothy Thompson

(57) ABSTRACT

At least one exemplary embodiment is directed to an ophthalmic image pickup apparatus that can separate and display image segments, where the image segments are assigned various priority levels for display, of an ophthalmic image according to the various priority levels.

7 Claims, 8 Drawing Sheets

OPHTHALMIC IMAGE PICKUP APPARATUS, OPHTHALMIC IMAGE PICKUP METHOD AND OPHTHALMIC IMAGE PROCESSING SYSTEM

BACKGROUND OF THE INVENTION

1. Field of the Invention

The present invention relates to an image display technique for an ophthalmic image pickup apparatus, and more particularly relates, though not exclusively, to an image display technique for a fundus camera.

2. Description of the Related Art

In a conventional ophthalmic image pickup apparatus (e.g., a fundus camera), an image pickup device (e.g., an area CCD) is used to record a fundus image, which is then recorded on a storage medium (e.g., an optical disk). The stored fundus image can then be displayed.

In another conventional system, a fundus image is transmitted to a personal computer (PC) (e.g., via USB port, or a network), so that the PC can record or display the fundus image.

Advancements in image pickup technology has outpaced information transfer and storage/access speeds so that too much time is required for recording, displaying and transferring a fundus image. Therefore, in order to reduce the processing time, an image compression technique, such as JPEG, is employed, or as discussed in Japanese Patent Laid-Open Publication No. Hei 6-98859, only required data, selected from among fundus image data, are transmitted.

SUMMARY OF THE INVENTION

At least one exemplary embodiment is directed toward aiding ophthalmic diagnosis by displaying various portions of a fundus image in a particular order. Where the particular order can be arranged to be displayed the portions having the highest priority.

At least one exemplary embodiment facilitates using a setup mode switch, where a fundus image that was photographed in advance is displayed on a photographed image monitor. Additionally, a grid-shaped area that is divided into image segments is displayed by a character synthesizer. A program control waits until the user employs an area setup switch to select one of several divided areas. When the user has selected an area, program control waits until the user employs a priority level setup switch to designate a priority level for the selected area. When the user designates the priority level, the area is displayed in a color that differs from a color representing the selected state and that is consonant with the priority level. After the priority level is designated, the priority level for the selected area is stored in nonvolatile memory. The above-described process is repeated until it is determined that the priority level setup mode switch has been pressed.

At least one exemplary embodiment is directed to a technique for an ophthalmic image pickup apparatus (e.g., a fundus camera), that can display images more efficiently than a conventional system.

At least one exemplary embodiment is directed to an ophthalmic image pickup apparatus, where the ophthalmic image pickup apparatus includes: an image pickup unit, configured to photograph a fundus image; an image dividing unit, configured to divide the fundus image into image segments; an image segment priority level setup unit, configured to set priority levels for the image segments; and an image segment recording unit, configured to record, for the individual image segments, position information relative to the original image and the priority levels.

In order to achieve the aforementioned object, the present invention provides an ophthalmic image pickup apparatus that is technically characterized by including image pickup means configured to pick up a fundus image to obtain image data; designating means configured to designate an objective of an image pickup operation performed by the image pickup means; image dividing means configured to divide the image data into image segments in accordance with the objective designated by the designating means; priority level setting means configured to set priority levels for the image segments divided by the image dividing means in accordance with the objective designated by the designating means; and recording means configured to record position information and the priority level of each of the image segments divided by the image dividing means, the position information indicating a position of the image segment within the image data.

At least one method of an ophthalmic image pickup method, in accordance with at least one exemplary embodiment, includes: an image pickup step of photographing a fundus image; an image dividing step of dividing the fundus image into image segments; an image segment priority level setup step of setting priority levels for the image segments; and an image segment recording step of recording, for the individual image segments, position information relative to the original image and the priority levels.

At least one further exemplary embodiment is directed to an ophthalmic image processing system where the ophthalmic image processing system includes: an image pickup unit, configured to photograph a fundus image; an image dividing unit, configured to divide the fundus image into image segments; an image segment priority level setup unit, configured to set priority levels for the image segments to be obtained by division; a transmission unit, configured to transmit position information for the individual image segments relative to the original image, the priority levels of the image segments and the image segments; a reception unit, configured to receive the image segments, the position information relative to the original image and the priority levels; an image segment recording unit, configured to record, for the individual image segments, the position information relative to the original image and the priority levels; and an image display unit, configured to display the image segments in priority level order.

At least one exemplary is directed to an ophthalmic image processing system where the ophthalmic image processing system includes: an image pickup unit configured to photograph a fundus image; an image segment priority level setup unit, configured to set priority levels for a plurality of areas in the fundus image; an image dividing unit, configured to divide the areas that are set in image segments; a transmission unit, configured to transmit position information for the individual image segments relative to the original image, the priority levels of the image segments and the image segments; a reception unit, configured to receive the image segments, the position information relative to the original image and the priority levels; an image segment recording unit, configured to record, for the individual image segments, the position information relative to the original image and the priority levels; and an image display unit, configured to display the image segments in priority level order.

At least one further exemplary embodiment is directed to an ophthalmic image pickup apparatus where the sizes of the at least two individual image segments obtained by the image dividing unit are changed according to whether an operating mode is set for normal photography or for enlarged photography. Note that the operating mode can be set by a user (e.g., using a switch) or automatically (e.g., auto focusing).

Other features of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments of the invention.

DESCRIPTION OF THE EMBODIMENTS

Figure 1:
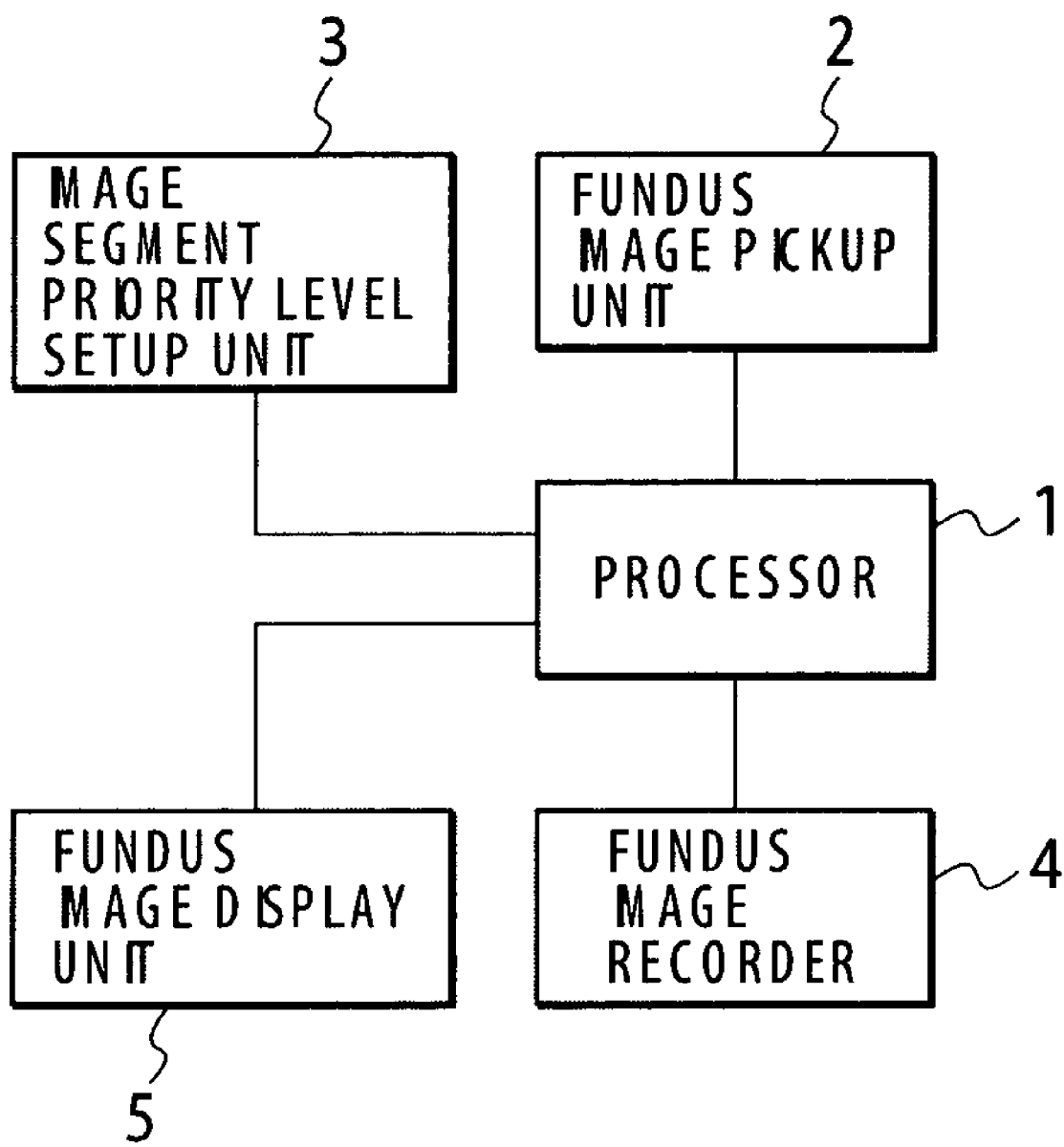
FIG. 1 illustrates a functional block diagram of a first exemplary embodiment.

The following description of exemplary embodiment(s) is merely illustrative in nature and is in no way intended to limit the invention, its application, or uses.

Exemplary embodiments can be operatively connected to various imaging devices (e.g., electronic cameras, camcorders, digital still cameras, film cameras, broadcast cameras, other imaging devices as known by one of ordinary skill, and equivalents).

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally exemplary embodiments are not limited to ophthalmic image pickup apparatus (e.g., optical photographic systems), for example, the system can be designed for use with fault detection systems using visual methods of fault detection and other wavelength image pickup apparatus, for example infrared and other wavelength imaging systems. Additionally, exemplary embodiments can be used with non-digital systems as well as digital systems (e.g., photographic systems using CCDs), for example a film image pickup apparatus can be used to obtain an image and then a scanning system can digitize the film image. The digitized film image can then be subject to the procedures discussed herein in accordance with at least one exemplary embodiment.

Notice that similar reference numerals and letters refer to similar items in the following figures, and thus once an item is defined in one figure, it may not be discussed or further defined in the following figures.

Exemplary embodiments will now be described in detail in accordance with the accompanying drawings.

Exemplary Embodiment 1

FIG. 1 illustrates a functional block diagram for a first exemplary embodiment. A processor 1 can control the image pickup apparatus. The image pickup apparatus comprises: a fundus image pickup unit 2, which can store a photographed fundus image in an image memory (e.g., RAM, SDRAM, optical disc, other memory storage mediums as know by one of ordinary skill in the relevant arts and equivalents); an image segment priority level setup unit 3, which can designate a priority level for each image segment of the photographed fundus image and can record the designated information in a memory (not shown); a fundus image recorder 4, which can record the fundus image segments in the priority level order set by the image segment priority level setup unit 3; and a fundus image display unit 5, which can display, in the priority level order, the image segments recorded by the fundus image recorder 4, all of which can be connected to the processor 1 (e.g., Pentium processor, Risc Processor, or any other type of processor as know by one of ordinary skill in the relevant arts and equivalents).

Figure 2:
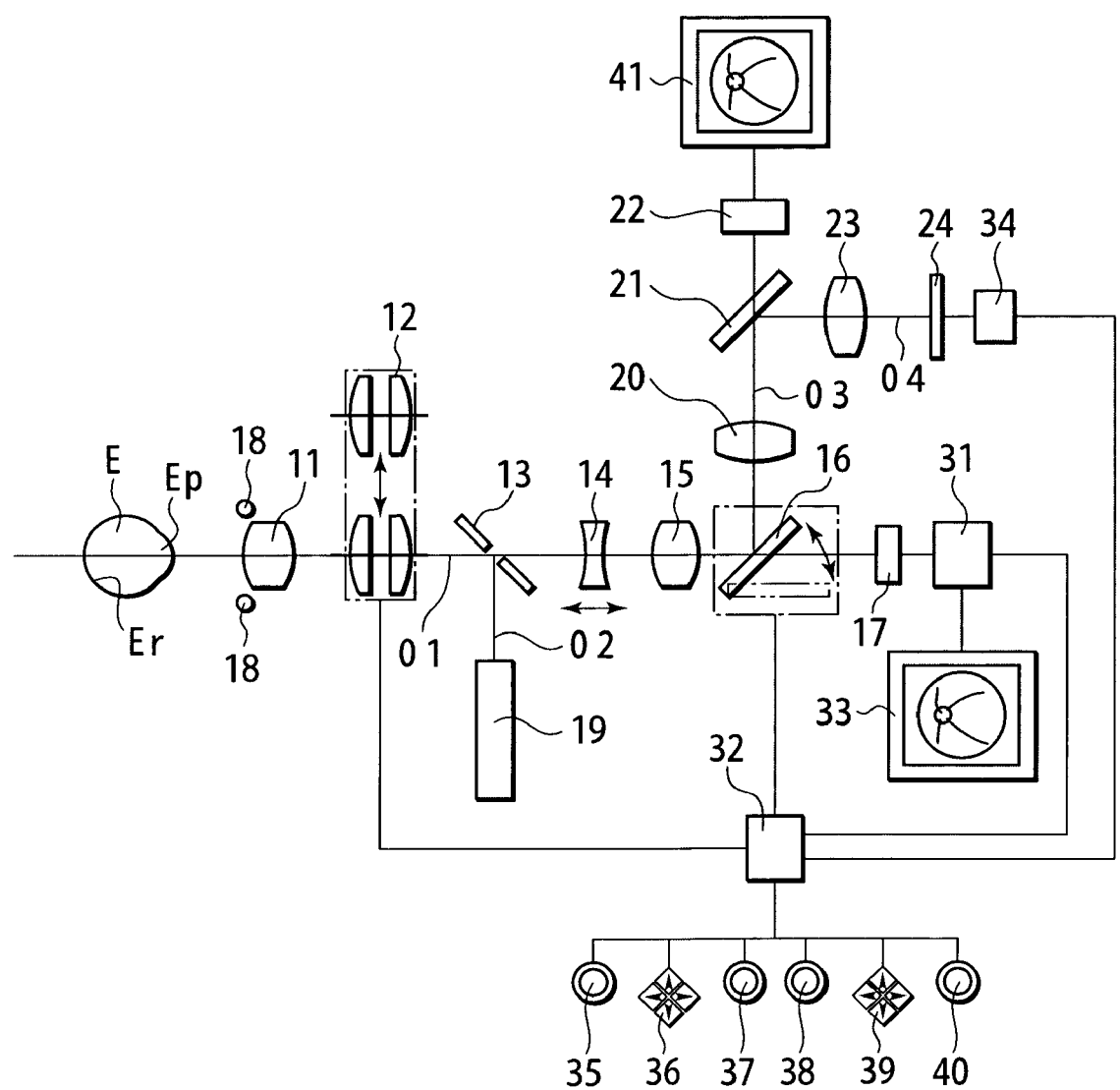
FIG. 2 illustrates a diagram showing an apparatus configuration.

FIG. 2 illustrates a diagram showing the arrangement of a fundus image pickup unit 2 in accordance with at least one exemplary embodiment. The fundus image pickup apparatus comprises: an object lens 11 facing an eye E to be examined; a detachable, front eye portion observation lenses 12; a perforated mirror 13 that has, in a portion containing a hole, a photographic diaphragm; a focus lens 14 that can be moved, in the direction of the eye, along an optical path O1 to adjust the focus; a photographing lens 15; a switching mirror 16 that can be located along the optical path O1 during the observation period and can be retracted, outside the optical path O1, at the moment a photograph is taken; an image pickup sensor unit 17 arranged along the optical path O1; and a light source 18, which can be used for front eye portion illumination and which can emit infrared light, can be arranged in the vicinity of the object lens 11.

Along an optical path O2 substantially perpendicular to the optical path O1, along which the perforated mirror 13 is mounted, a fundus luminaire 19 is arranged. The fundus luminaire 19 emits infrared light onto the fundus during observation of the fundus, or emits visible light thereon during the photographing of the fundus.

A field lens 20, a half mirror 21 and an observation sensor unit 22 can be arranged along the path of light O3 reflected by the switching mirror 16.

Figure 3:
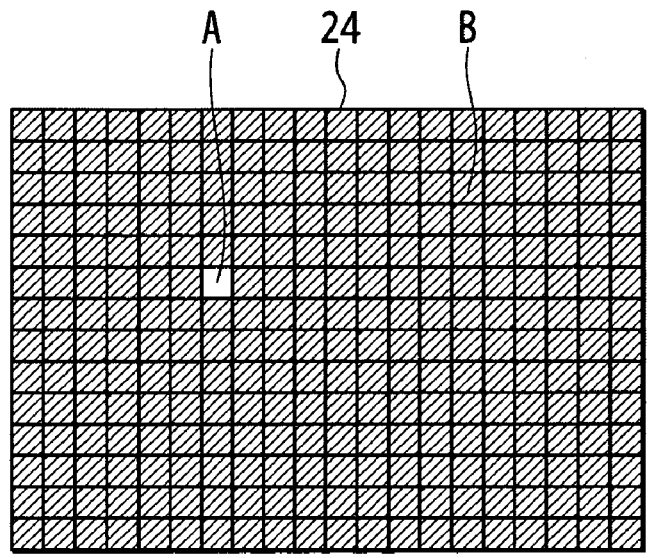
FIG. 3 illustrates an explanatory diagram showing a liquid crystal element.

Along the optical path O4 in the direction of the reflection from the half mirror 21, a lens 23 and a fixed gaze target indicator 24, which displays a fixed gaze target, can be arranged. The fixed gaze target indicator 24 can include a backlight and a liquid crystal element wherein multiple cells, for example as shown in FIG. 3, are arranged in the shape of a matrix. Whether to permit or prevent the transmission of light can be set for the individual cells.

The output terminal of the image pickup sensor unit 17 is operatively connected through the image memory 31 to a controller 32 and a photographed image monitor 33. In at least one further exemplary embodiment, the image pickup sensor unit 17 is connected directly to the controller 32. The switching mirror 16, the front eye portion observation lenses 12, a front eye portion/fundus select switch 35, a fixed gaze target moving switch 36, a photographing switch 37, a priority level setup mode switch 38, an area setup switch 39 and a priority level setup switch 40 are also operatively connected to the controller 32. In at least one exemplary embodiment, the fixed gaze target controller 34 is connected to the fixed gaze indicator 24. In addition, the output terminal of the observation sensor unit 22 can be connected to an observed image monitor 41.

With this arrangement, first, in the front eye observation state, an image pickup operator schematically positions the eye E to be examined and the object lens 11. In the front eye observation state, the front eye portion observation lenses 12 are inserted into the optical path O1, the light source 18 for front eye portion illumination is turned on and the switching mirror 16 is located along the optical path O1.

For front eye portion illumination, an image of the front eye portion formed by reflected infrared light, from the light source 18, is passed through the object lens 11, the front eye portion observation lenses 12, the hole in the perforated mirror 13, the focus lens 14 and the photographing lens 15, and is reflected by the switching mirror 16. The reflected light (e.g., traveling along O3) is passed through the field lens 20 and the half mirror 21, and is focused on the pickup face of the observation sensor unit 22. Then, the image of the front eye portion obtained by the observation sensor unit 22 (e.g., obtained through photoelectric conversion), is displayed on the observed image monitor 41.

The image pickup operator moves a stage (not shown) on which the fundus image pickup unit 2 is mounted while viewing the image of the front eye portion, and adjusts the position of the eye E to be examined and the position of the object lens 11.

When the eye E to be examined and the object lens 11 have been positioned in this manner, an alignment indicator signal is received by the controller 32 (e.g., from depression of the front eye portion/fundus select switch 35), the controller 32 detects the alignment indicator signal, and turns off the light source 18 for front eye portion illumination. The front eye portion observation lenses 12 are retracted (e.g., after the light source 18 is turned off) and removed from the optical path 01, and the fundus luminaire 19 emits infrared light along optical path O2.

Infrared light emitted by the fundus luminaire 19 is reflected by the mirror portion in the periphery of the perforated mirror 13, and the reflected light passes through the object lens 11 and illuminates fundus Er through pupil Ep. The fundus image obtained by the illumination is passed from the pupil Ep through the object lens 11, the hole in the perforated mirror 13, the focus lens 14 and the photographing lens 15, and is reflected by the switching mirror 16. The reflected light is transmitted through the field lens 20, and is passed further, through the half mirror 21, and focused on the pickup face of the observation sensor unit 22. Finally, the fundus image obtained by the illumination is displayed on the observed image monitor 41.

The controller 32 permits (e.g., in parallel with the described procedures) the fixed gaze target controller 34 to turn on the backlight of the fixed gaze target indicator 24, so that a fixed gaze target is presented to the eye E. The transmission of light can be controlled by the controller to permitted transmission only to predesignated cells of the liquid crystal element. As illustrated in FIG. 3, the fixed gaze indicator 24 can define a transmitting cell as a light opening portion A, and a non-transmitting cell as a light blocking portion B. Light that is emitted by the backlight and transmitted through the opening portion A passes through the lens 23 and is reflected by the half mirror 21 toward optical path O1. The reflected light passes through the field lens 20 and is reflected by the switching mirror 16. The reflected light is thereafter transmitted through the photographing lens 15, the focus lens 14, the hole in the perforated mirror 13 and the object lens 11, and reaches the fundus Er through the pupil Ep of the eye E to be examined. That is, for a person to be examined, whose pupil Ep is positioned along the optical path O1 of the object lens 11, the image of the opening portion A is presented as a fixed gaze target in a solid black background.

Figure 4:
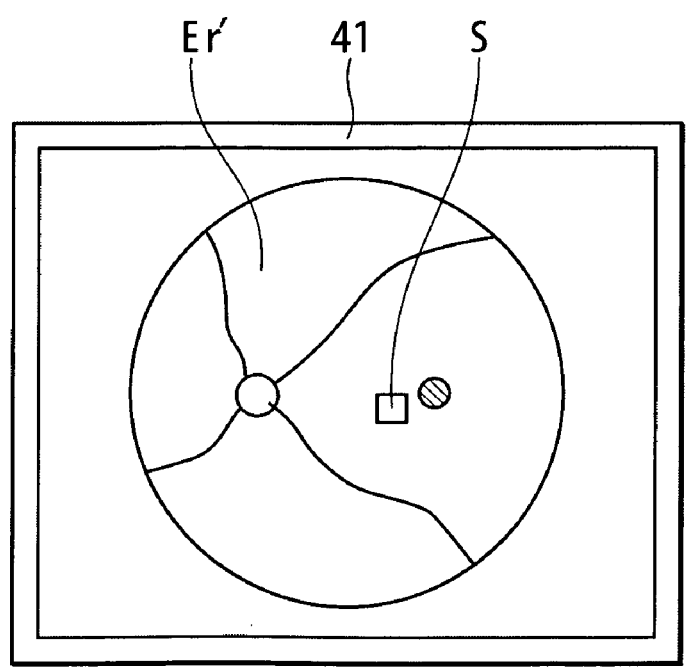
FIG. 4 illustrates an explanatory diagram for the presentation of a fixed gaze target, on a monitor, for an observed image.

Furthermore, as illustrated in FIG. 4, a character S, indicating the position of a fixed gaze target presented to the eye E to be examined, is synthesized with the fundus image by a character synthesizer (not shown), and the synthesized image Er' is displayed on the observed image monitor 41. The image pickup operator manipulates the fixed gaze moving switch 36, while viewing the fundus image Er' and the character S displayed on the observed image monitor 41, moves the position of the fixed gaze target provided by the cell and guides the line of sight of the examinee in order to photograph a desired portion.

After the desired portion to be photographed has been obtained through this manipulation, the image pickup operator initiates a photographic signal to be sent to the controller 32 (e.g., by pressing the photographing switch 37) to photograph a fundus. The obtained image can then be stored in the image memory 31.

Figure 5:
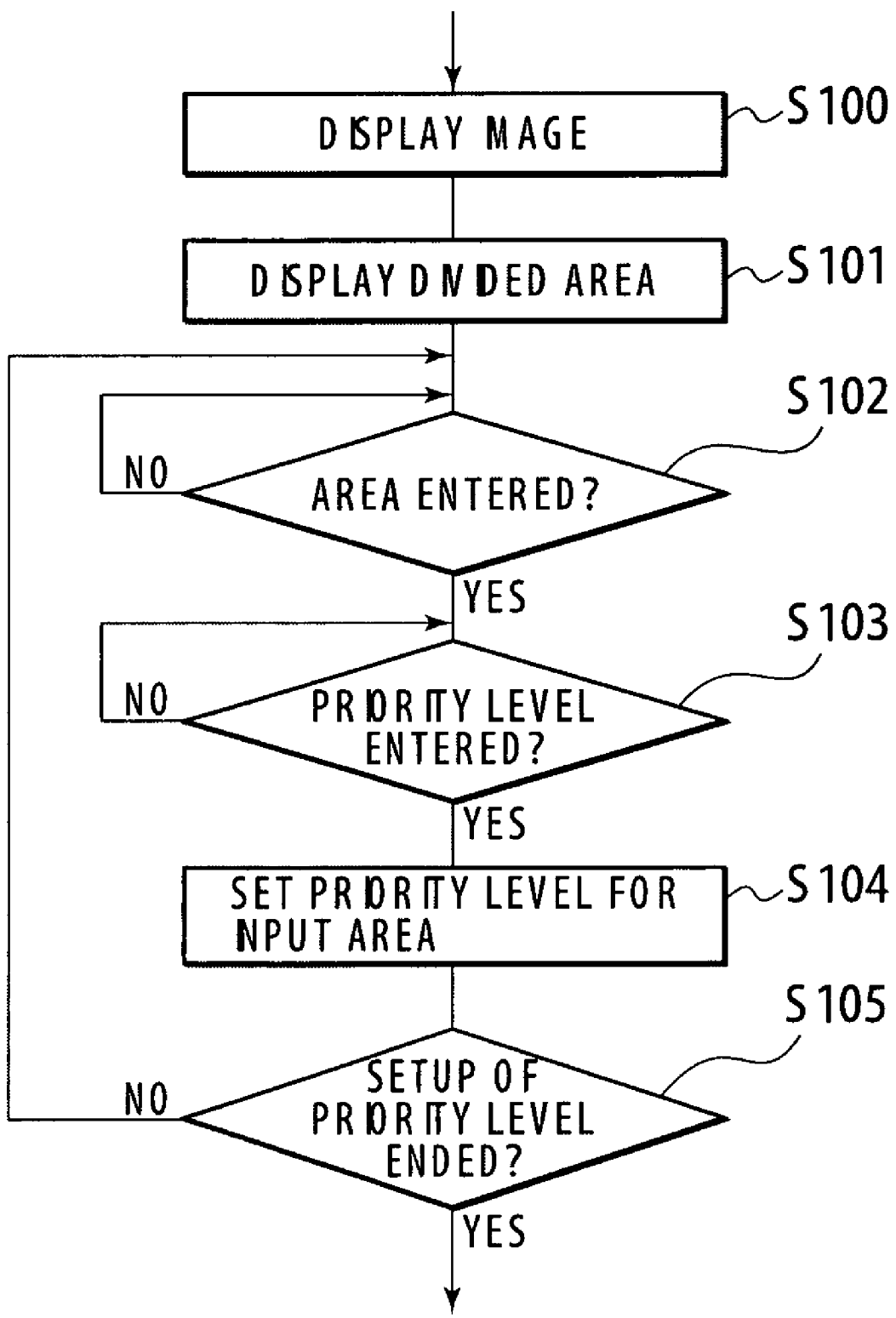
FIG. 5 illustrates a flowchart showing a process for setting the priority levels for image segments.
Figure 6:
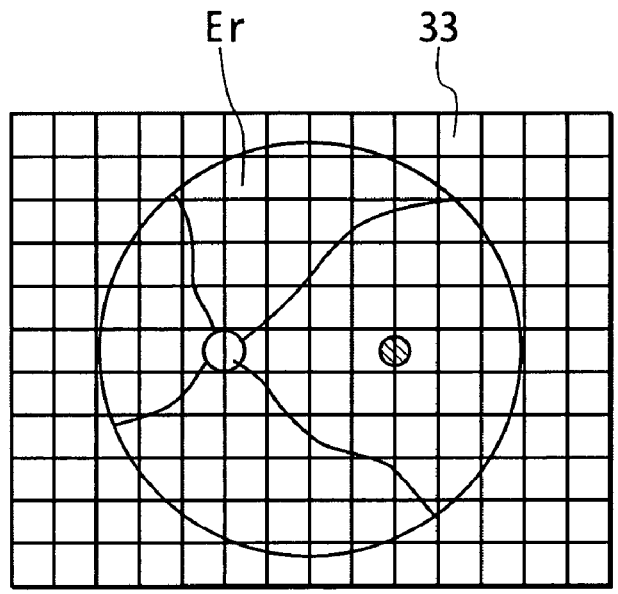
FIG. 6 illustrates an explanatory diagram showing image segments.

FIG. 5 illustrates a flowchart showing the operation of the image segment priority level setup unit 3. When a setup mode signal is received by the controller 32 (e.g., when a user presses the priority level setup mode switch 38), at step S100, the fundus image Er' that was photographed in advance is displayed on the photographed image monitor 33. At step S101, a grid-like area shown in FIG. 6, which is divided into image segments, is displayed on image monitor 33 by a character synthesizer (not shown).

The size of each image segment is in accordance with a setup value for a system that is stored in nonvolatile memory (not shown). Upon receipt by the controller 32 of an image segment size change signal (e.g., upon the depression of an image segment size change switch (not shown)), the size of the image segment can be changed by reading from the nonvolatile memory multiple setup values for the system. Further, by sending another signal (e.g., using a switch (not shown)), a user can change the setup value for the size of the image segment. In addition, and in accordance with the state of a variable magnification switch (not shown), the size of each image segment can also be designated for a normal photographing process and for an enlargement photographing process.

At step S102, the controller 32 queries whether it has received an area setup signal (e.g., a user employs the area setup switch 39 to select one of the grid areas, where the area setup switch 39 can be a cursor key, a mouse or a joy stick). The area selected by the user (i.e., and subsequently sent to the controller 32 as an area setup signal) is displayed by using a semitransparent color representing a selected state. Multiple areas can also be selected (e.g., by using the area setup switch 39).

Figure 7:
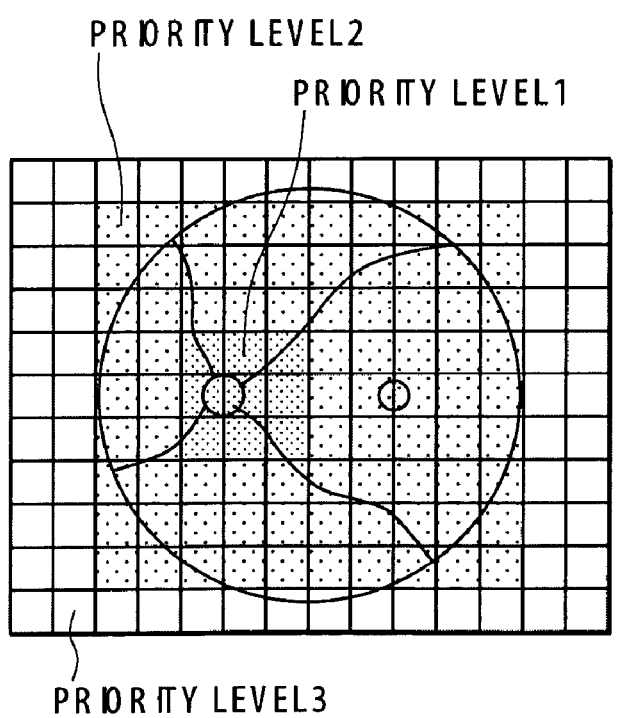
FIG. 7 illustrates an explanatory diagram showing the setup of priority levels for image segments.

When the user has selected an area, at step S103, the controller 32 waits until the user sends a priority level setup signal (e.g., a user employs the priority level setup switch 40) to designate a priority level for the selected area. When the user designates the priority level, the area can be displayed with various colors or grayscale in accordance to priority, for example as illustrated in FIG. 7 (with a dotted patterns used to symbolize color) by using a semitransparent color that differs from the semitransparent color indicating the selected state and is consonant with the priority level. In accordance with at least one exemplary embodiment, although not shown, a list of display colors for the individual priority levels can be displayed on the photographed image monitor 33 by a character synthesizer (not shown). The priority level may be designated either as high/middle/low, or as a numeral value. When a numeral value is employed, a high priority level may be represented by either a large value or a small value, as in FIG. 7, for example, wherein a small value is used to represent a high priority level.

After the user has designated the priority level, the priority level of the area selected at step S104, i.e., the priority level of the image segment, can be stored in the nonvolatile memory (not shown). The above process is repeated until it is determined, at step S105, that another setup mode signal has been received by the controller 32 (e.g., the priority level setup mode switch 38 has been pressed).

Figure 8:
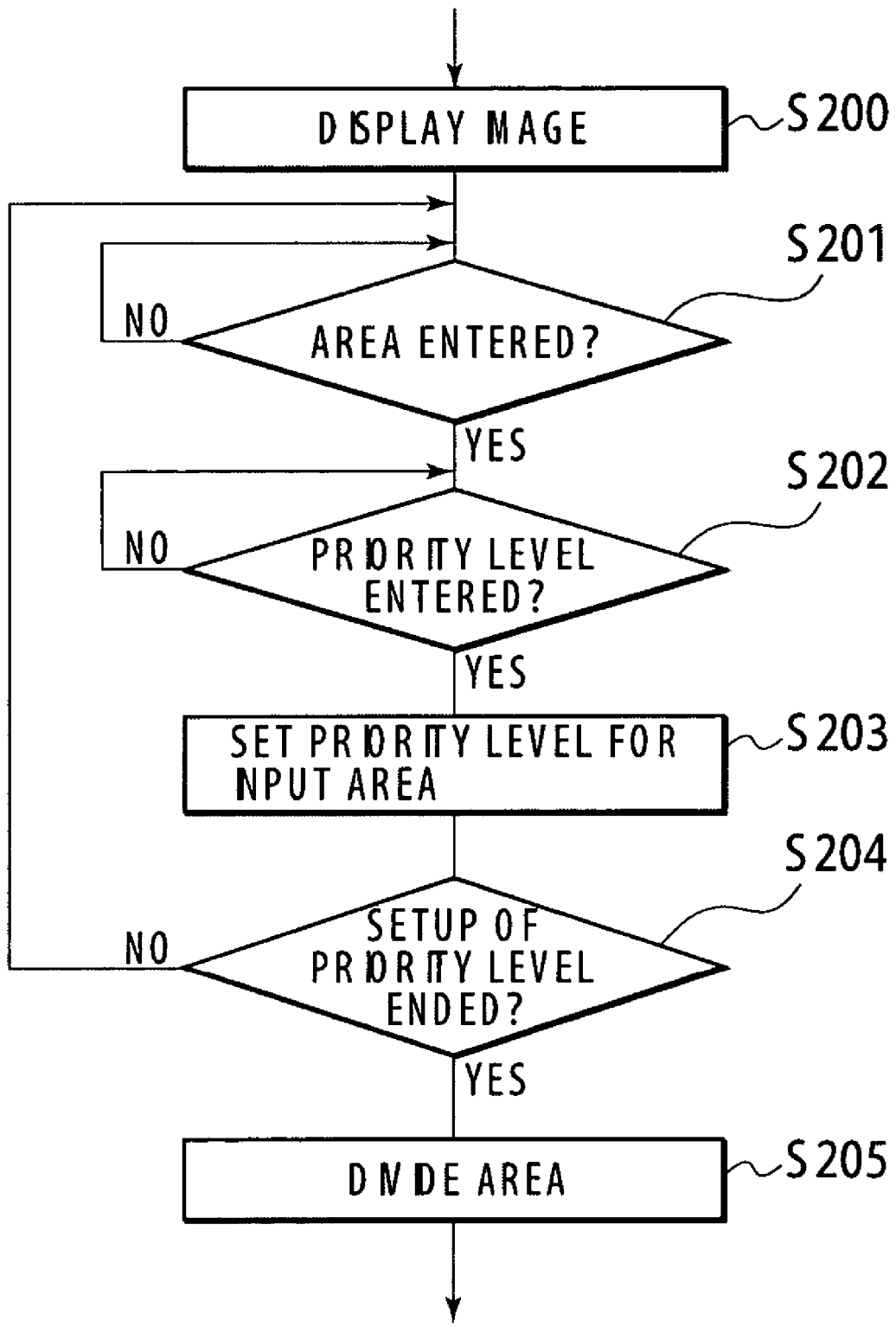
FIG. 8 illustrates a flowchart showing a process for setting the priority levels for image segments.
Figure 9:
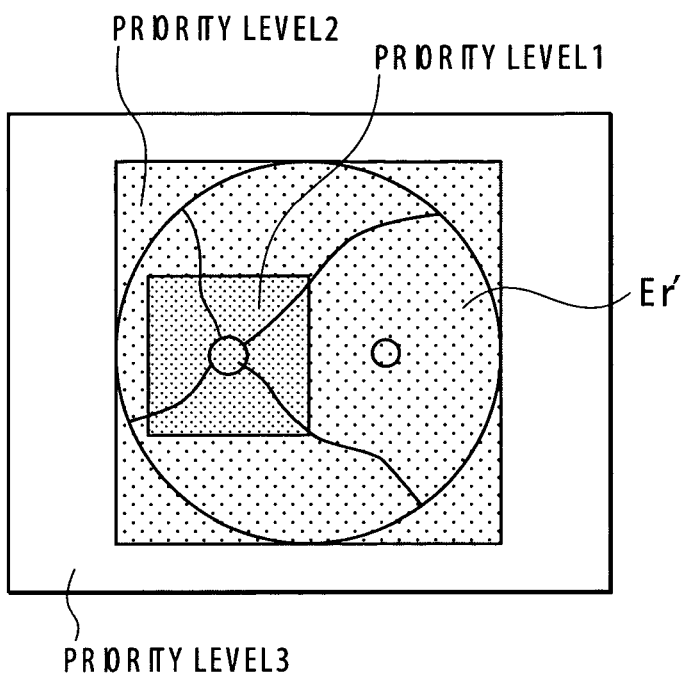
FIG. 9 illustrates an explanatory diagram showing the setup of priority levels for image segments.

Furthermore, as illustrated in the flowchart in FIG. 8, instead of displaying a grid-shaped area that is divided into image segments, a user may send a setup mode signal (e.g., employ the area setup switch 39) to designate a rectangular area, as shown in FIG. 9, and can send a priority level setup signal (e.g., employ the priority level setup switch 40) to designate a priority level for this rectangular area. For example, when at step S200 the user presses the priority level setup mode switch 38, a fundus image that was photographed in advance is displayed on the photographed image monitor 33.

At step S201, controller 32 waits until the user employs receives a setup mode signal, (e.g., the area setup switch 39 is used to select an area). In this case, the user can designate a rectangular area as an arbitrary position. The area selected by the user can be displayed using colors or grayscales (e.g., a semitransparent color) that represents the selected state. Multiple areas can also be selected (e.g., using the area setup switch 39).

At step S202, the controller 32 waits until a priority level setup signal is received, corresponding to a particular selected area (e.g., the user employs the priority level setup switch 40 to designate a priority level for the selected area). When a priority level setup signal is received (e.g., when the user designates the priority level), the area is displayed, as shown in FIG. 9, for example, using a semitransparent color/grayscale that differs from the semitransparent color/grayscale representing the selected state, and one that is consonant with the priority level. In at least one exemplary embodiment, the list of display colors for the individual priority levels be displayed on the photographed image monitor 33 using a character synthesizer (not shown). The priority level can be designated either as high/middle/low, or as a numeral value. When a numeral value is employed, a high priority level can be either a large value or a small value, as in FIG. 9, for example, wherein a small value is used to represent a high priority level.

After the designation of the priority level, the priority level of the area selected at step S203 is stored in the nonvolatile memory (not shown). The above-described process is repeated until it is determined, at step S204, that a priority setup mode signal has been received by the controller 32 (e.g., the priority level setup mode switch 38 has been pressed).

Figure 10:
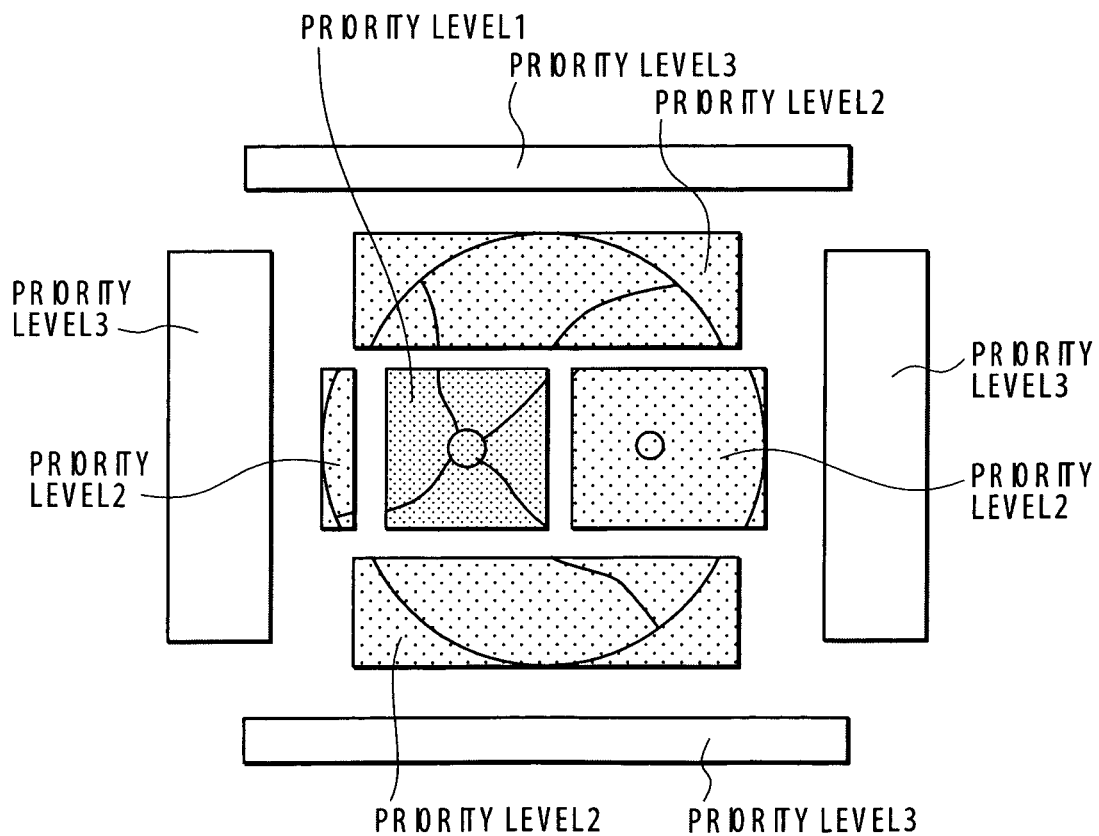
FIG. 10 illustrates an explanatory diagram showing the division of an area into image segments.

When a priority setup mode signal has been received by the controller 32 at step S205 (e.g., the user presses the priority level setup mode switch 38), the fundus image is divided in accordance with an area selected (e.g., selected by the user). For example, FIG. 10 illustrates a divided fundus image consonant with the selected areas of image segment and their respective selected priority levels. When the rectangular areas, having designated priority levels, overlap, either the priority level of the rectangular area that has been designated the latest may be employed for the overlapped portion, or a higher priority level may be employed.

The method for designating an area and thereafter setting a priority level has been explained while referring to the flowcharts in FIGS. 5 and 8. However, the priority level may be selected first and then the area may be designated. Furthermore, a user may, for example, designate a priority level for an optic disk, for a macula lutea, for a vascular area, for a fundus portion other than an optic disk/a macula lutea/a vascular area and for an aperture mask area. And after their images have been photographed, these areas may be extracted by image processing and the priority levels designated in accordance with the ratios of the extracted areas relative to the grid areas that have been divided into image segments.

In addition, a user may designate a procedure having a diagnostic purpose, such as medical checkups, an examination for glaucoma or an examination for macular degeneration, and the diagnostic area and the priority level may be automatically set (e.g., without user designation) in accordance with the purpose of the diagnostic procedure. For example, in the case of a fundus image pickup for an examination performed for a lifestyle-related illness, a fundus image is photographed so that the optic disk of the eye to be examined and the center of the macula lutea come at the center of an image. Therefore, a priority level of "1" is assigned for an image segment that includes the optic disk and the macula lutea, a priority level of "2" is assigned for an image segment that includes the vascular area, a priority level of "3" is assigned for an image segment for a fundus portion that does not include the optic disk/macula lutea/ vascular area, and a priority level of "4" is assigned for an image segment that includes most of the aperture mask. It should be noted that in this particular example a small value represents a high priority level.

Likewise, in the case of fundus photography performed for a glacoma examination, a fundus image can be photographed so that the optic disk of the eye to be examined comes at the center of an image. Therefore, a priority level of "1" is assigned for an image segment that includes the optic disk, a priority level of "2" is assigned for an image segment that includes a vascular area, a priority level of "3" is assigned for an image segment that does not include the optic disk/vascular area, and a priority level of "4" is assigned for an image segment that includes most of the aperture mask. Again, it should be noted that in this particular example a small value represents a high priority level.

Similarly, in the case of fundus photography for an examination for macula lutea degenerative symptoms, a fundus image is photographed so that the macula lutea comes at the center of an image. Therefore, a priority level of "1" is assigned for an image segment that includes the macula lutea, a priority level of "2" is assigned for an image segment that includes the vascular area, a priority level of "3" is assigned for an image segment for a fundus portion that does not include the macula lutea/vascular area, and a priority level of "4" is assigned for an image segment that includes most of the aperture mask.

The fundus image recorder 4 can record an image segment, and may compress this image segment using JPEG, for example. For each image segment of a photographed image designated by the image segment priority level setup unit 3, the size of the image segment, the original image name, the position information relative to the original image and the priority level can be recorded, with the image segment, as collateral information for the image. In at least one exemplary embodiment the serial number of the apparatus or a time photograph can be employed to provide the original image name, so that the original image can be uniquely identified.

When various information is to be recorded as collateral information for an image, the image segment name can be provided (e.g., original image name+image segment number), or a series of image segments that constitute the original image can be recorded in the same directory, so that the series of image segments constituting the original image can be easily identified.

The size of an image segment, the original image name, the position information relative to the original image and the priority level can be recorded in a file separate from that employed for the image segment. A different file can be prepared for each image segment, or information for all the image segments of the original image can be recorded in a single file.

When a fundus image that was obtained in advance is displayed on the fundus image display unit 5, the size of image segments, the original image name, the position information relative to the original image and the priority level can be read from the collateral information included in the file for the image segments, or from a file separate from the one for the image segments. Additionally, the image segments can be displayed in the priority level order.

Image segments for which the resolutions, are low, may also, as a whole, be recorded by the fundus image recorder 4, and when these recorded images are to be reproduced, the image segment having the lowest resolution can be displayed first and the remainder of the image segments can be displayed, across the screen, in the priority level order.

In at least one exemplary embodiment, the display of the fundus image photographed by the fundus image pickup unit 2, is read from the image memory 31.

Figure 11:
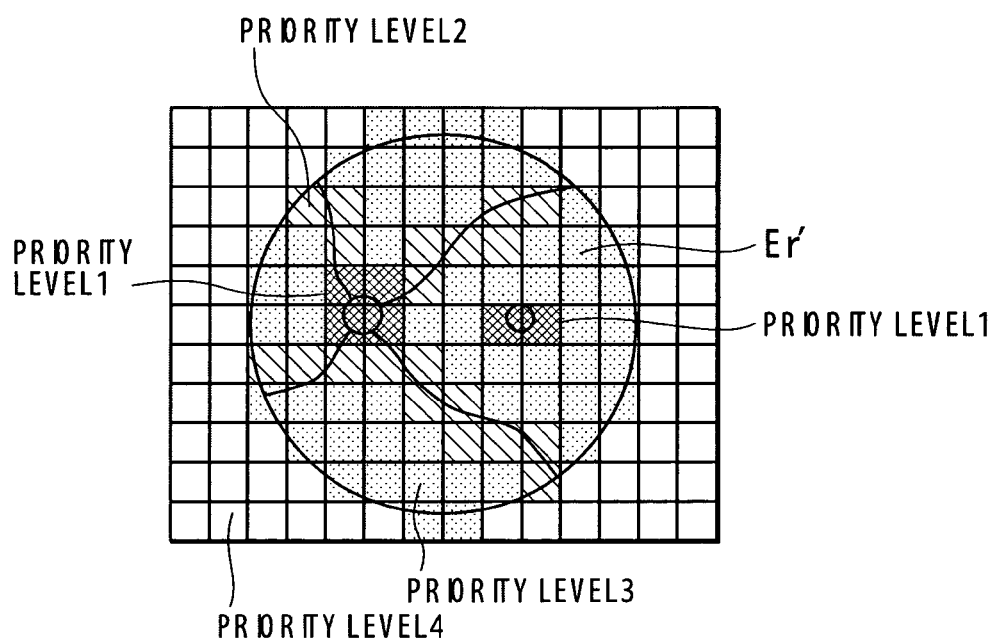
FIG. 11 illustrates an explanatory diagram showing the setup of priority levels for image segments.

In the non-limiting example discussed above with reference to FIG. 9, a rectangular area can be designated. Further exemplary embodiments can designate a variety of areas and thus are not limited to designating only rectangular areas. For example FIG. 11 illustrates an image in accordance with at least one exemplary embodiment where four priority levels, of various shapes, have been designated (e.g., priority levels 1-4).

Exemplary Embodiment 2

Figure 12:
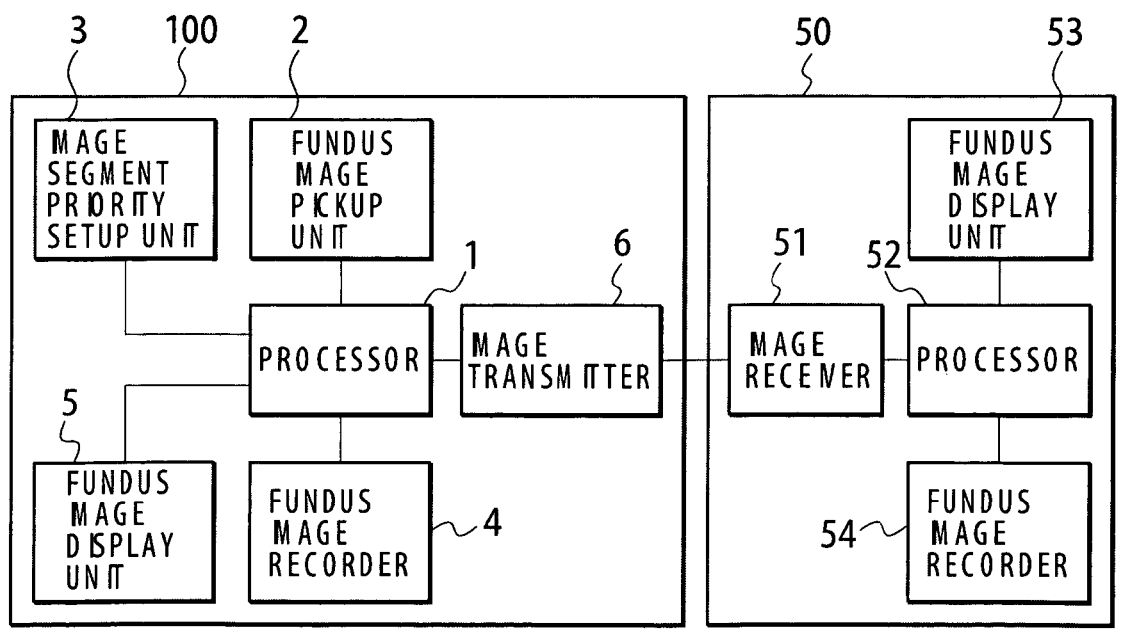
FIG. 12 illustrates a functional block diagram for a second exemplary embodiment.

The ophthalmic image pickup apparatus, of the first exemplary embodiment, that records and displays image segments has been described. FIG. 12 illustrates a functional block diagram for a second exemplary embodiment, wherein a personal computer (PC) 50 is additionally provided for the ophthalmic image pickup apparatus shown in FIG. 1. In the ophthalmic image pickup apparatus of the second exemplary embodiment, an image transmitter 6 is connected to a processor 1 and is also connected to an image receiver 51 of the PC 50. The output terminal of the image receiver 51 is operatively connected to a processor 52. A fundus image display unit 53 and a fundus image recorder 54 are connected to the processor 52. At least one exemplary embodiment is directed to an ophthalmic image processing system where an image segment is transmitted to the PC 50, and where an image segment is also recorded and displayed by the PC 50.

An image transmitter 6 transmits image segments recorded by a fundus image recorder 4 to the PC 50 (e.g., in the priority level order). When a variety of information is not included in the collateral information for image segments, but is recorded in separate files, these files can also be transmitted. When separate files are prepared for the individual image segments, first, the files, and then, the image segments can be transmitted in consonance with the priority levels. The image transmitter 6 can transmit image segments generated by the processor 1, instead of image segments recorded by the fundus image recorder 4.

Based on the sizes of the image segments and the position information relative to the original image, the fundus image display unit 53 assembles image segments in accordance with the order in which received and displays the image received in real time. Since the image segments are received in the descending order of their priority levels, the image segments are displayed beginning with the highest priority level. Other exemplary embodiments can display image segments according to their priority levels in the reverse order. The ophthalmic image pickup apparatus can transmit an image having a low resolution before transmitting image segments, and the PC 50 can display the image having the low resolution first and then display the image segments received in the priority level order.

To display a photographed image that was previously received, the fundus image display unit 53 can read the sizes of image segments, the original image name, the position information relative to the original image and the priority levels from the collateral information included for the image segments, or from a separate file provided for the image segments, and displays the image segments in accordance with the priority levels. When an image having a low resolution is received from the ophthalmic image pickup apparatus and recorded, the image having the low resolution can be displayed first, and image segments can be displayed atop it in accordance with their priority levels.

In the functional block diagram in FIG. 12, the image segment priority level setup unit 3 is arranged in the ophthalmic image pickup apparatus 100. However, the image segment priority level setup unit 3 can be arranged in the PC 50 and a transmitter provided for the PC 50, and a receiver can be provided for the ophthalmic image pickup apparatus 100, so that information designated by the PC 50 can be transmitted to the ophthalmic image pickup apparatus 100. Thus, in other exemplary embodiments the various elements (e.g., 1-5) can be located in, what is referred to as, PC 50.

According to the exemplary embodiments, the priority levels can be set for the individual image segments of the fundus image and this information can be recorded, so that the fundus image is displayed beginning with the image segment having the highest priority level. Therefore, a diagnosis can be made beginning at the portion having the highest priority level, i.e., the portion for which the diagnosis is required, and the diagnosis time can be reduced.

Most of the processing in the exemplary embodiments can be provided by using a computer program. The above exemplary embodiments can also be provided in the following manner. The computer program code (also referred to as "program" or "program code") can be stored on a storage medium, the software performing the functions of the above exemplary embodiments, and can be supplied to a system or an apparatus. The computer (the CPU or the MPU) of the system or the apparatus reads and executes the program code stored on the storage medium.

In this case, the program code read from the storage medium can provide the functions of the above-described exemplary embodiments, and the storage medium on which the program code is stored constitutes at least one exemplary embodiment. The storage medium on which the program code is stored can be, for example, a floppy disk, a hard disk, an optical disk, a magneto-optical disk, a CD-ROM, a magnetic tape, a nonvolatile memory card or a ROM.

At least one exemplary embodiment is directed to a technique for an ophthalmic image pickup apparatus, such as a fundus camera, that increases the efficiently of displays images.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

This application claims priority from Japanese Patent Application No. 2004-292502 filed on 5 Oct. 2004, which is hereby incorporated by reference herein in its entirety.

What is claimed is:

1. An ophthalmic image pickup apparatus comprising:
an image pickup unit configured to pick up a fundus image to obtain image data;
a designating unit configured to designate an objective of an image pickup operation performed by the image pickup unit;
an image dividing unit configured to divide the image data into image segments in accordance with the objective designated by the designating unit; a priority level setting unit configured to set priority levels for the image segments divided by the image dividing unit in accordance with the objective designated by the designating unit;
and a recording unit configured to record position information and the priority level of each of the image segments divided by the image dividing unit, the position information indicating a position of the image segment within the image data.

2. An ophthalmic image pickup apparatus according to claim 1, further comprising an image display unit configured to display the image segments recorded by the recording unit in the order of the priority levels.

3. An ophthalmic image pickup apparatus according to claim 1, further comprising a transmitting unit configured to transmit the position information, the priority levels, and the image segments.

4. An ophthalmic image pickup apparatus according to claim 1, wherein the image segments divided by the image dividing unit are changed in size between normal photography and enlarged photography.

5. An ophthalmic image pickup apparatus comprising:
an image pickup unit configured to pick up a fundus image to obtain image data; a priority-region setting unit configured to set a plurality of regions having priority levels in the image data;
an image dividing unit configured to divide the regions set by the priority-region setting unit into image segments; and
a recording unit configured to record position information and the priority level of each of the image segments divided by the image dividing unit, the position information indicating a position of the image segment within the image data.

6. An ophthalmic image processing system comprising:
an image pickup unit configured to pick up a fundus image to obtain image data;
a priority-region setting unit configured to set a plurality of regions having priority levels in the image data; an image dividing unit configured to divide the regions set by the priority-region setting unit into image segments;
a transmitting unit configured to transmit position information and the priority levels, the position information indicating a position of each image segment within the image data;
a receiving unit configured to receive the image segments, the position information within the image data, and the priority levels transmitted from the transmitting unit; a recording unit configured to record the position information and the priority level of each image segment; and
a image display unit configured to display the image segments in the order of the priority levels.

7. An ophthalmic image processing system according to claim 6, wherein the image segments divided by the image dividing unit are changed in size between normal photography and enlarged photography.

* * * * *